United States Patent
Ishida et al.

(10) Patent No.: US 8,203,018 B2
(45) Date of Patent: Jun. 19, 2012

(54) PROCESSES FOR PRODUCING HYDROXYALKYL (METH) ACRYLATE

(75) Inventors: Tokumasa Ishida, Himeji (JP); Hiroyuki Takaki, Himeji (JP); Masahiro Uemura, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 643 days.

(21) Appl. No.: 11/659,370

(22) PCT Filed: Aug. 5, 2005

(86) PCT No.: PCT/JP2005/014421
§ 371 (c)(1),
(2), (4) Date: Feb. 5, 2007

(87) PCT Pub. No.: WO2006/013971
PCT Pub. Date: Feb. 9, 2006

(65) Prior Publication Data
US 2008/0154060 A1    Jun. 26, 2008

(30) Foreign Application Priority Data
Aug. 6, 2004    (JP) .................................. 2004-231379

(51) Int. Cl.
C07C 67/26    (2006.01)
C07C 59/00    (2006.01)
(52) U.S. Cl. ........................................ 560/209; 562/579
(58) Field of Classification Search .................. 560/200, 560/205, 209, 224
See application file for complete search history.

(56) References Cited

U.S. PATENT DOCUMENTS

| | | | | |
|---|---|---|---|---|
| 3,875,211 | A * | 4/1975 | Steckler ........................ | 560/209 |
| 4,365,081 | A * | 12/1982 | Shimizu et al. ............... | 560/209 |
| 6,984,751 | B2 | 1/2006 | Takaki et al. | |
| 7,045,651 | B2 | 5/2006 | Ishida et al. | |
| 7,214,817 | B2 | 5/2007 | Ishida et al. | |
| 2004/0030180 | A1 | 2/2004 | Takaki et al. | |

FOREIGN PATENT DOCUMENTS

| | | | |
|---|---|---|---|
| EP | 1 389 610 | | 2/2004 |
| EP | 1389610 | A * | 2/2004 |
| JP | 2003-40837 | | 2/2003 |
| JP | 2003-40838 | | 2/2003 |
| JP | 1 344 764 | | 9/2003 |
| JP | 2003-267929 | | 9/2003 |
| JP | 2003-300932 | * | 10/2003 |
| JP | 2004-10602 | | 1/2004 |
| JP | 2004-010603 | | 1/2004 |
| JP | 2004-75559 | | 3/2004 |
| JP | 2004-123577 | | 4/2004 |
| JP | 2004182634 | * | 7/2004 |
| JP | 2004244364 | * | 9/2004 |

OTHER PUBLICATIONS

JP2004244364, Shintani et al., English translation (20 pages).*
JP2004182634, Takagi et al., English translation (18 pages).*
JP2003300932, Kamimura et al., English translation (11 pages).*
European Office Action issued Jan. 17, 2011 in corresponding European Application No. EP 05 768 905.1.
Taiwan Office Action issued Apr. 15, 2011 in corresponding Taiwan Patent Application No. 099103140, with English translation.
Japanese Notice of Reasons for Refusal (with English translation) issued May 17, 2011 in corresponding Japanese Application No. 2006-531592.
Japanese Notice of Reasons for Refusal (with English translation) issued Aug. 2, 2011 in corresponding Japanese Application No. 2006-531592.

* cited by examiner

*Primary Examiner* — Yate K Cutliff
(74) *Attorney, Agent, or Firm* — Wenderoth, Lind & Ponack, L.L.P.

(57) ABSTRACT

Processes for producing a hydroxyalkyl(meth)acrylate which comprise reacting (meth)acrylic acid with an alkylene oxide in the presence of a catalyst. A first process is characterized in that the amount of the acid ingredient is kept, on calculation, at 0.010 or more in terms of molar ratio to the catalyst present in the liquid reaction mixture and that the liquid reaction mixture from which the hydroxyalkyl(meth)acrylate has been distilled off is used in the subsequent reaction. A second process is characterized in that a dialkylene glycol mono (meth)acylate is supplied to the reaction system to cause the dialkyleneglycol mono(meth)acylate to coexist in the liquid reaction mixture.

3 Claims, No Drawings

PROCESSES FOR PRODUCING HYDROXYALKYL (METH) ACRYLATE

FIELD OF THE INVENTION

The present invention relates to a method for producing hydroxyalkyl(meth)acrylate by a reaction of (meth)acrylic acid and alkylene oxide in the presence of a catalyst.

BACKGROUND ART

Catalysts are usually used in methods for producing hydroxyalkyl(meth)acrylate by a reaction of (meth)acrylic acid and alkylene oxide. General recognition is that homogeneous catalysts such as chromium compounds, iron compounds, and the like are preferred as the above-described catalysts. In recent years, while consideration for environment, health, and the like requires severer regulations for various wastewater, waste gas emission, and the like, there arise a strong concern for problems in potential harmfulness of disposal of catalysts, and thus desired is decrease, as much as possible, of amounts of the catalysts used in producing processes.

On the other hand, the above-described methods for producing hydroxyalkyl(meth)acrylate easily form, as by-products of impurities, dialkylene glycol mono(meth)acrylates (hereinafter, may be referred to as "biadduct") as biadducts of alkylene oxide, leading to decrease in yield of targeted products. Therefore, all possible suppression of formation of the by-products has conventionally be en desired. In the producing method of this hydroxyalkyl(meth)acrylate, since independent introduction of alkylene oxide is accompanied by possible risk, (meth)acrylic acid is beforehand introduced. For example, Japanese Patent Application Laid-Open No. 2004-10602 proposes a process of suppressing by-production of the biadduct, wherein a higher concentration of catalysts to an amount of (meth)acrylic acid is selected in a reaction liquid at the time of reaction commencement with introduction of the alkylene oxide.

DESCRIPTION OF THE INVENTION

As a recycling process of using a catalyst once used for a subsequent reaction, proposed are: a process of use of a reaction liquid to the subsequent reaction by means of additional supply of a fresh (new) catalyst to the reaction liquid after refined by distillation, (for example, refer to Japanese Patent Application No. 2002-234630); a process of use after almost perfect reactivation of a catalyst by means of alkali treatment of a reaction liquid after distillation refining (for example, refer to Japanese Patent Application No. 2003-128292), and the like.

However, both of the above-mentioned techniques of recycling of catalysts and by-production suppression of the biadduct are susceptible to improvement for simplicity of process, or production costs. In detail, the processes of additional supply of fresh catalysts among recycling technologies of catalysts need a certain amount of catalysts for assistance of inactivated catalysts or catalysts having deteriorated activity, and therefore the methods have still insufficient effect in view of the reduction effect of the amount of catalysts to be used. In addition, although the process of alkali treatment is excellent in reduction of the amount of catalysts used, and reactivation of the catalysts, it needs a process of treatment with alkalis, and therefore it has still some room of improvement in simplification of the process. In addition, the suppression technique of by-production of the biadduct sometimes needs further suppression effect, and therefore it requires realization of further improvement in yield of hydroxyalkyl(meth)acrylate as a targeted product and suppression of by-production of the biadduct. For this reason, there has been needed catalyst recycling technologies allowing simpler processes avoiding complexity, and catalyst recycling technologies providing decrease in alkali treatment costs.

Then, the present invention aims at providing a process for manufacturing hydroxyalkyl(meth)acrylate allowing lower production costs.

In order to solve the above-mentioned problems, wholehearted investigations have been performed by the present inventors. In the course of the investigations, there has been found out that use of a novel measure for maintaining a condition that an amount of acid components, such as (meth) acrylic acid, constantly falls in a specific molar ratio range, with respect to an amount of a catalyst in a reaction liquid can effectively suppress inactivation itself of the catalyst used for the reaction, and that use of the catalyst without any additional treatment can make a subsequent reaction fully exhibit catalytic activity, and can furthermore suppress the amount of the catalyst used and process costs in the recycling technology of the above-mentioned catalysts, leading to solution of the problems described above. As a result, in a preferable embodiment, omission of additional supply of a new catalyst or reactivation of the catalyst after used was also attained. In the process for preparation of hydroxyalkyl(meth)acrylate by means of a reaction of (meth)acrylic acid and alkylene oxide, the reaction may progress due to residual unreacted alkylene oxide in a cooling process of termination of the reaction, in a standby process period before distillation refining (evaporation) of the targeted product, and in a distillation refining process and the like. The present inventors found out that almost all consumption or perfect consumption of acid components, such as (meth)acrylic acid in a reaction liquid by what is called a progress of additional reaction and the like, makes all of or partial amount of catalysts inactivated and makes impossible return of the catalysts to an activated condition. And, the amount of the catalyst and the acid component in the reaction liquid are studied based on this information, and found out was that simple maintenance of a calculative ratio (molar ratio) of the amount of the acid component to the amount of the catalyst so as to satisfy a specific range allows effective suppression of inactivation of the catalyst, and allows efficient recycling.

Furthermore, with respect to suppression technique of by-production of the above-mentioned biadduct, also found out was that formation of the above-mentioned by-product can be suppressed much more effectively by use of a novel measure allowing coexistence of the biadduct in the reaction liquid by means of supply of dialkylene glycol mono(meth)acrylate into the reaction system (preferably supply of dialkylene glycol mono(meth)acrylate is beforehand performed before reaction), and thereby yield of hydroxyalkyl(meth)acrylate as a targeted product improved, leading to solution of the problems mentioned above. In chemical reactions generally called an equilibrium reaction, it is well known that admission of coexistence of a by-product in a reaction liquid can effectively suppress formation thereof. However, since alkylene oxide as a source compound cannot be obtained from the biadduct formed with by-production reaction in a reaction of (meth)acrylic acid and alkylene oxide, this reaction may not be understood as an equilibrium reaction. This will be obvious from a fact that a three membered-rings of alkylene oxide as an epoxy compound once opened cannot be closed to an original form. Here, the present inventors found out that although the reaction between (meth)acrylic acid and alkylene oxide is a non equilibrium reaction, causing of coexistence of the biadduct as a by-product by means of separate supply (preferably supply of dialkylene glycol mono(meth)acrylate is beforehand performed before reaction) can effectively suppress formation of thereof, resulting in a high yield of hydroxyalkyl(meth)acrylate as a targeted product.

The present invention has thus been completed. Of processes for producing hydroxyalkyl(meth)acrylate according to the present invention, a first process is a process for producing hydroxyalkyl(meth)acrylate by a reaction between (meth)acrylic acid and alkylene oxide in the presence of a catalyst, the process maintains an amount of an acid component to an amount of the catalyst to give a value calculatively not less than 0.010 in terms of a molar ratio in a reaction liquid, the process using the reaction liquid after evaporation of hydroxyalkyl(meth)acrylate therefrom for a subsequent reaction.

A second process is a process for producing hydroxyalkyl(meth)acrylate by a reaction between (meth)acrylic acid and alkylene oxide in the presence of a catalyst, the process supplying dialkylene glycol mono(meth)acrylate into a reaction system to cause coexistence of the dialkylene glycol mono(meth)acrylate in a reaction liquid. In addition, preferable embodiments include incorporation of a part of the first process to the second process. That is, maintenance of a condition of giving a value calculatively not less than 0.010 in terms of a molar ratio of the amount of the acid component to the amount of the catalyst in the reaction liquid will maintain a condition where the amount of the acid component as (meth)acrylic acid in the reaction liquid satisfies a range of a specific molar ratio to the amount of the catalyst, and therefore inactivation of the catalyst itself used for the reaction can effectively be suppressed. Furthermore, preferable embodiments also include reuse of the reaction liquid after evaporation of hydroxyalkyl(meth)acrylate therefrom to a reaction between (meth)acrylic acid and alkylene oxide as in the first process.

In the second process, the coexisting amount of the dialkylene glycol mono(meth)acrylate is calculatively 2 to 100 in terms of a molar ratio with respect to the amount of the catalyst in the reaction liquid, the dialkylene glycol mono(meth)acrylate can beforehand be supplied before the reaction, and the dialkylene glycol mono(meth)acrylate included in the reaction liquid after evaporation of hydroxyalkyl(meth)acrylate therefrom can be used for supply into the system of reaction.

In the first process and second process, the catalyst can be a homogeneous catalyst including chromium compounds.

BEST MODE FOR CARRYING-OUT THE INVENTION

The present invention will, hereinafter, be described in detail, aspects of the present invention is not intended to be limited by these descriptions, and exemplification other than the following descriptions may also suitably be modified and may be carried out in a range without impairment of an object of the present invention. In a process for producing hydroxyalkyl(meth)acrylate according to the present invention (hereinafter, may be referred to as a producing method of the present invention), as described above, either of the first and the second processes produce hydroxyalkyl(meth)acrylate by a reaction between (meth)acrylic acid and alkylene oxide in the presence of a catalyst. The first and second processes may be applied for any of publicly known or already proposed processes for producing hydroxyalkyl(meth)acrylate by a reaction between (meth)acrylic acid and alkylene oxide.

The (meth)acrylic acid usable for the producing process of the present invention represents an acrylic acid and/or a methacrylic acid.

The alkylene oxides usable for the producing process of the present invention are not especially limited. For example, alkylene oxides having from 2 to 6 carbons are preferably used, and alkylene oxides having from 2 to 4 carbons are more preferably used. In detail, ethylene oxide, propylene oxide, butylene oxide, and the like may be mentioned. Especially, ethylene oxide and propylene oxide are preferred.

The recycling method of use of the catalyst once used in the subsequent reaction of the present invention includes a preferable embodiment wherein use of ethylene oxide as the alkylene oxides may exhibit especially higher effect for suppressing inactivation of the catalyst. In addition, although use of propylene oxide may exhibit effective result for suppressing inactivation of the catalyst, it cannot easily cause inactivation of the catalyst compared with a case of ethylene oxide. However, also in propylene oxide, application of the producing process of the present invention beneficially makes multiple recycling times of the catalyst. Furthermore, also in butylene oxide, effect of suppressing inactivation of the catalyst may similarly be exhibited.

In the producing process of the present invention, the relationship of amounts between the total amount of supply of (meth)acrylic acid and the total amount of supply of alkylene oxide is not limited in a reaction between (meth)acrylic acid and alkylene oxide, and alkylene oxide is preferably not less than 1 mole to 1 mole of (meth)acrylic acid, more preferably 1.0 to 10 moles, still more preferably 1.0 to 5.0 moles, especially preferably 1.0 to 3.0 moles, most preferably 1.0 to 2.0 moles. In the above-mentioned relationship of the amounts, an amount of alkylene oxide less than 1.0 mole to 1 mole of (meth)acrylic acid may possibly impair progress of the reaction, furthermore leading to possible decrease in reaction conversion and to possible increase in by-products. On the other hand, an excessive amount of alkylene oxide in the above-mentioned relationship of amounts, especially an amount more than 10 moles to (meth)acrylic acid 1 mole, needs a recovery process of alkylene oxide and the like, causing a possibility of economical disadvantage.

Catalysts usable in the producing process of the present invention include all homogeneous catalysts soluble in a reaction liquid including (meth)acrylic acid and alkylene oxide. Although the catalysts are not limited, the catalysts, in detail, preferably include at least one kind selected from the group consisting of chromium (Cr) compounds, iron (Fe) compounds, yttrium (Y) compounds, lanthanum (La) compounds, cerium (Ce) compounds, tungsten (W) compounds, zirconium (Zr) compounds, titanium (Ti) compounds, vanadium (V) compounds, phosphorus (P) compounds, aluminum (Al) compounds, and molybdenum (Mo) compounds, the catalysts being homogeneous catalysts soluble in the reaction liquid. Especially, homogeneous catalysts including chromium (Cr) compounds and/or iron (Fe) compounds soluble in the reaction liquid are more preferred, homogeneous catalysts, including chromium (Cr) compounds, soluble in the reaction liquid are still more preferred, and homogeneous catalysts, consisting of chromium (Cr) compounds, soluble in the reaction liquid are most preferred. Especially in the first process described later, use of homogeneous catalysts, comprising chromium (Cr) compounds, soluble in the reaction liquid, as a catalyst, advantageously gives much more remarkable results, and use of homogeneous catalysts, consisting of chromium (Cr) compounds, soluble in the reaction liquid gives more preferred results.

The chromium (Cr) compounds are not limited, and include compounds having a chromium (Cr) atom(s) within the molecule and being soluble in the reaction liquid. In detail, there may be mentioned chromium chlorides, chromium acetylacetonates, chromium formates, chromium acetates, chromium octanoates, chromium isooctanates, chromium acrylates, chromium methacrylates, bichromate-of-soda, chromium dibutyldithiocarbamate, and the like.

The iron (Fe) compounds are not limited, and include compounds having an iron (Fe) atom(s) within the molecule and being soluble in the reaction liquid. In detail, there may be mentioned iron powder, iron chlorides, iron formates, iron acetates, iron acrylates, iron methacrylates, and the like.

The yttrium (Y) compounds are not limited, and include compounds having a yttrium (Y) atom(s) within the molecule and being soluble in the reaction liquid. In detail, there may be mentioned yttrium acetylacetonate, yttrium chloride, yttrium acetate, yttrium nitrate, yttrium sulfate, yttrium acrylate, yttrium methacrylate, and the like.

The lanthanum (La) compounds are not limited, and include compounds having a lanthanum (La) atom(s) within the molecule and being soluble in the reaction liquid. In detail, there may be mentioned lanthanum acetylacetonate, lanthanum chloride, lanthanum acetate, lanthanum nitrate, lanthanum sulfate, lanthanum acrylate, lanthanum methacrylate, and the like.

The cerium (Ce) compounds are not limited, and include compounds having a cerium (Ce) atom(s) within the molecule and being soluble in the reaction liquid. In detail, there may be mentioned cerium acetylacetonate, cerium chloride, cerium acetate, cerium nitrate, cerium sulfurate, cerium acrylate, cerium methacrylate, and the like.

The tungsten (W) compounds are not limited, and include compounds having a tungsten (W) atom(s) within the molecule and being soluble in the reaction liquid. In detail, there may be mentioned tungsten chloride, tungsten acrylate, tungsten methacrylate, and the like.

The zirconium (Zr) compounds are not limited, and include compounds having a zirconium (Zr) atom(s) within the molecule and being soluble in the reaction liquid. In detail, there may be mentioned zirconium acetylacetonate, zirconium chloride, zirconium acetate, zirconium nitrate, zirconium sulfurate, zirconium acrylate, zirconium methacrylate, zirconium butoxide, zirconium propoxide, zirconyl chloride, zirconyl acetate, zirconium nitrate, zirconyl acrylate, zirconyl methacrylate, and the like.

The titanium (Ti) compounds are not limited, and include compounds having a titanium (Ti) atom(s) within the molecule and being soluble in the reaction liquid. In detail, there may be mentioned titanium chlorides, titanium nitrates, titanium sulfurates, titanium methoxide, titanium ethoxide, titanium propoxide, titanium isopropoxide, titanium acrylate, titanium methacrylate, and the like.

The vanadium (V) compounds are not limited, and include compounds having a vanadium (V) atom(s) within the molecule and being soluble in the reaction liquid. In detail, there may be mentioned vanadium acetylacetonate, vanadium chloride, vanadium naphthenate, vanadium acrylate, vanadium methacrylate, and the like.

The phosphorus (P) compounds are not limited, and include compounds having a phosphorus (P) atom(s) within the molecule and being soluble in the reaction liquid. In detail, there may be mentioned alkylphosphines, such as trimethylphosphine, tributyl phosphine, trioctyl phosphine, triphenyl phosphine, tritoluoyl phosphine, 1,2-bis(diphenylphosphine)ethane, and the like, and quaternary phosphonium salts, such as (meth)acrylate salts thereof and the like.

The aluminum (Al) compounds are not limited, and include compounds having an aluminum (Al) atom(s) within the molecule and being soluble in the reaction liquid. In detail, there may be mentioned aluminum acetylacetonate, aluminum chloride, aluminum acetate, aluminum nitrate, aluminum sulfate, aluminum ethoxide, aluminum isopropoxide, aluminum acrylate, aluminum methacrylate, and the like.

The molybdenum (Mo) compounds are not limited, and include compounds having a molybdenum (Mo) atom(s) within the molecule and being soluble in the reaction liquid. In detail, there may be mentioned molybdenum chloride, molybdenum acetate, molybdenum acrylate, molybdenum methacrylate, and the like.

As catalysts usable for the producing process of the present invention, there may preferably be mentioned catalysts (amine compounds combined-use type) including homogeneous catalysts comprising: at least one kind selected from the group consisting of chromium (Cr) compounds, iron (Fe) compounds, yttrium (Y) compounds, lanthanum (La) compounds, cerium (Ce) compounds, tungsten (W) compounds, zirconium (Zr) compounds, titanium (Ti) compounds, vanadium (V) compounds, phosphorus (P) compounds, aluminum (Al) compounds, and molybdenum (Mo) compounds, the homogeneous catalysts being soluble in the reaction liquid; and amine compounds.

The above-mentioned amine compounds are not limited as long as they are compounds having an amine functional group within the molecule, and in detail, there may be mentioned homogeneous amine compounds, such as cyclic amines, e.g. trialkylamines and pyridine, and the quaternary salts thereof. Combined use of the above-mentioned amine compounds can synergistically improve catalytic activity, leading to improvement in both of reaction conversion and reaction selectivity.

Although the amount of catalysts used in the producing process of the present invention is not limited, for example, in use of the above-described homogeneous catalyst, soluble in the reaction liquid, including at least one kind selected from the group consisting of chromium (Cr) compounds and the like (a case without combined use with amine compounds), the homogeneous catalyst is preferably used so as to give 0.01 to 10 mole % to (meth)acrylic acid, more preferably 0.02 to 5 mole %, and still more preferably 0.04 to 3 mole %. The amount used less than 0.01 mol % lengthens a reaction period due to a lower rate of reaction, and provides possibility of raising production costs. The amount used exceeding 10 mole % may raise the reaction selectivity of by-products.

Furthermore, in the above-described combined use of catalysts with amine compounds, the catalyst is preferably used so that the amount of the amine compounds used may give 0.01 to 10 mole % to (meth)acrylic acid, more preferably 0.02 to 5 mole %, and still more preferably 0.04 to 3 mole %. The amount of the homogeneous catalyst, soluble in the reaction liquid, including at least one kind selected from the group consisting of chromium (Cr) compounds and the like is preferably 0.01 to 5 mole %, more preferably 0.02 to 5 mol %, and still more preferably 0.04 to 3 mole %. The amount used of less than 0.01 mole % may possibly not exhibit synergistic effects, and the amount used exceeding 5 mole % may possibly raise production costs.

The reaction between (meth)acrylic acid and alkylene oxide represented by the producing process of the present invention is not limited, and it may be performed in so-called a batch type reaction (batch reaction), or in a successive reaction (continuous reaction). The batch reaction may easily be completed, and in this case since the reaction does not need facilities for recovery of unreacted (meth)acrylic acid or alkylene oxide, it is preferably economical. Since the successive reaction does not need an occupancy period of a reactor, such as raw material introduction, temperature raise, cooling, draw out, and standby, as in the case of the batch reaction, the reaction may advantageously improve productivity.

In case of carrying out the producing process of the present invention by the batch reaction, in detail, the reaction is progressed by suitable supply of a catalyst, (meth)acrylic acid, and alkylene oxide to a reactor, and the reaction is generally terminated when the amount of residual (meth)acrylic acid in the reaction liquid reaches a desired amount. In addition, the reaction between (meth)acrylic acid and alkylene oxide is an exothermic reaction. The reaction starts from commencement of coexistence of these raw material compounds in the presence of the catalyst in the reactor, and the reaction can be terminated by forcing of the temperature of the reaction liquid in this reactor to a temperature lower than a predetermined reaction temperature by cooling and the like. In supplying methods (supplying order, amount of supply, and the like) of (meth)acrylic acid and alkylene oxide in case of operation by the batch reaction, in general, a part of or whole amount of only (meth)acrylic acid is supplied to the reactor in an early stage, and then into the reactor a remainder of the (meth) acrylic acid and alkylene oxide are concurrently or separately supplied, or only alkylene oxide is supplied. However, supplying method is not limited to the method described above, and for example, a part of or whole amount of alkylene oxide may also be supplied in the early stage.

In supply of (meth)acrylic acid and alkylene oxide in case of operation by the batch reaction, both of collective supply, and successive supply (continuous supply and/or intermittent supply) may be adopted, and the collective supply is preferably adopted for a portion for initial supply, and the successive supply is preferably adopted for a portion of subsequent supply. Here, the continuous supply represents a mode of a continuous supply performed little by little, and the intermittent supply represents a mode of supply divided into suitable number of times pulsed or intermittent. And the continuous supply may be progressed until termination of the supply at a fixed supply speed, and it may be progressed with at least one variation of speed during the reaction, or may be progressed with continuous and optional variations of speed itself. However, in variation of speed during the reaction, the speed is preferably decreased from the speed before shift.

In the case of continuous supply of alkylene oxide, in order to control the reaction temperature, preferably mentioned is also a method of changing a supply speed during the reaction so as to raise the speed (that is, the speed is raised from the speed before the change). Furthermore, preferably mentioned is a method allowing control to a preset temperature in such a manner that a solution temperature is raised with heat of reaction by continuous supply of alkylene oxide at a solution temperature predetermined temperature (for example, 1 degree C.) lower than the preset temperature.

Supply of (meth)acrylic acid and alkylene oxide to both or either of a liquid phase and a gas phase is not especially limited. However, since absorption of alkylene oxide contained in a reactant gas allows shift out of the range of inflammability, the (meth)acrylic acid is preferably supplied to the gas phase, and since vaporization can be controlled, the alkylene oxide is preferably supplied to the liquid phase.

Sometimes a vaporized reaction liquid may condense on a wall surface of the gas phase of the reactor and of a distilling column, and (meth)acrylic acid and hydroxyalkyl(meth)acrylate without a polymerization inhibitor may possibly give thermal residence thereon to form a polymer, and therefore the condensate (polymer may preferably be included) washed out with the reaction liquid including a below-mentioned polymerization inhibitor.

In the case of operation by the batch reaction, a period of time needed until termination of supply of whole amount of the (meth)acrylic acid and alkylene oxide is not limited, and the period of time may suitably be determined in consideration of a degree of completion of the reaction, production costs, and the like of the reaction.

In the case of operation by the successive reaction of the producing process of the present invention, in detail, the reaction is progressed by continuous supply of a catalyst, (meth)acrylic acid, and alkylene oxide to a reactor, and then the reaction is generally terminated by drawing the reaction liquid out of the reactor at a residence period where an amount of residual (meth)acrylic acid in the reaction liquid gives a desired amount. The reaction of (meth)acrylic acid and alkylene oxide is exothermic reaction as described above, the above-mentioned reaction starts when these raw material compounds continuously supplied into the reactor and a catalyst are forced to coexist, the above-mentioned reaction may be terminated when the temperature of the reaction liquid continuously drawn out from the reactor is lowered by cooling and the like to a temperature lower than a predetermined reaction temperature.

In the case of operation by the successive reaction, in supply mode (supplying order, amount of supply, and the like) of (meth)acrylic acid and alkylene oxide, a whole amount of (meth)acrylic acid and a whole amount of alkylene oxide are generally simultaneously supplied to the reactor, but the supply mode is not limited to the above-mentioned modes. For example, in the case of operation of reaction by use of two or more reactors, (meth)acrylic acid and alkylene oxide may be divided and supplied to each of the reactors, and only (meth)acrylic acid may be divided and supplied to each of the reactors.

In the case of operation by the successive reaction, sequential supply of (meth)acrylic acid and alkylene oxide is appropriate, and continuous supply at a fixed supply speed is especially preferred. In the case of reaction using two or more reactors, the molar ratio of alkylene oxide to (meth)acrylic acid is preferably closer to 1.0 in reactors positioned later in the divided reactors.

In either case of operation by the batch reaction, and of operation by the successive reaction of the producing process of the present invention (hereinafter, referred to as "in the case of operation by the batch reaction or the successive reaction"), (meth)acrylic acid and alkylene oxide may be supplied to the reactor at ordinary temperatures, or they may be supplied to the reactor after pre-heating to desired temperatures in order to avoid variation of the temperature of the reaction liquid in the point of time.

In the case of operation by the batch reaction or the successive reaction, when (meth)acrylic acid and alkylene oxide are simultaneously supplied, each of them may be supplied to the reactor from separate supply lines, or may be supplied to the reactor after blending in pipings (line mixer and the like), mixing tanks, and the like. However, since supply from separate supply lines may possibly cause partial uneven distribution of a molar ratio of alkylene oxide and (meth)acrylic acid in the reaction liquid, supply after preceding blending is preferred. In the case of supply from separate supply lines, the mode of supply (collective supply or successively supply), temperatures of raw material compounds to be supplied, supply speed, and the like between each raw material compound are not limited, and they may be identical, or different from each other.

In the case of operation by the batch reaction or the successive reaction, in general, the range of the reaction temperature is preferably 40 to 130 degrees C., and more preferably 50 to 100 degrees C. The above-mentioned reaction temperature less than 40 degrees C. may possibly make progress of reaction slower to a level without practicability, and the above-mentioned temperature more than 130 degrees C. may possibly increase a produced amount of by-products by polymerization of (meth)acrylic acid as a raw material compound or hydroxyalkyl(meth)acrylate as a targeted product. The system internal pressure during the reaction is dependent on kinds and mixing ratios of raw material compounds to be used, and generally the reaction is preferably performed under application of pressure. Reaction solvents may preferably be used for the purpose of milder progress of the reaction and the like. The reaction solvent is not limited, and commonly used solvents as reaction solvents, such as toluene, xylene, heptane, and octane, may be used.

The above-mentioned reaction (batch reaction and successive reaction) and distillation may be performed in the presence of polymerization inhibitors. Publicly known polymerization inhibitors may generally be used as a polymerization inhibitor, and they are not limited. For example, the polymerization inhibitors include: phenolic compounds, such as hydroquinone, methylhydroquinone, tert-butyl hydroquinone, 2,6-di-tert-butyl hydroquinone, 2,5-di-tert-butyl hydroquinone, 2,4-dimethyl-6-tert-butylphenol, and hydroquinone monomethyl ether, and the like; paraphenylene diamines, such as N-isopropyl-N'-phenyl-paraphenylene diamine, N-(1,3-dimethylbutyl)-N'-phenyl-paraphenylene diamine, N-(1-methylheptyl)-N'-phenyl-paraphenylene diamine, N,N'-diphenyl-paraphenylene diamine, N,N'-di-2-naphthyl paraphenylene diamine and the like; amine compounds, such as thiodiphenylamine and phenothiazine; copper dialkyl dithiocarbamates, such as copper dibutyl dithiocarbamate, copper diethyldithiocarbamate, copper dimethyldithiocarbamate and the like; nitroso compounds, such as nitrosodiphenylamine, isoamyl nitrite, N-nitrosocyclohexylhydroxylamine, N-nitroso-N-phenyl-N-hydroxylamine, and salts of the above-mentioned compounds and the like; N-oxyl compounds, such as 2,2,4,4-tetramethylazetidine-1-oxyl, 2,2-dimethyl-4,4-dipropylazetidine-1-oxyl, 2,2,5,5-tetramethyl pyrrolidine-1-oxyl, 2,2,5,5-tetramethyl-3-oxopyrrolidine-1-oxyl, 2,2,6,6-tetramethylpiperidine-1-oxyl, 4-hydroxy-2,2,6,6-tetramethylpiperidine-1-oxyl, 6-aza-7,7-dimethylspiro[4.5]decane-6-oxyl, 2,2,6,6-tetramethyl-4-acetoxy piperidine-1-oxyl, 2,2,6,6-tetramethyl-4-benzoyloxy piperidine-1-oxyl, 4,4',4"-tris-(2,2,6,6-tetramethylpiperidine-1-oxyl)phosphite, 4,4'-bis-(2,2,6,6-tetramethylpiperidine-1-oxyl)sebacate and the like; nitrogen oxides, such as nitrogen monoxide and nitrogen dioxide and the like. One kind of the polymerization inhibitor may be used, and two or more kinds may be used in combination. Oxygen may be used in combination in order to further increase polymerization preventive effect. The amount of addition of the polymerization inhibitor is preferably 0.0001 to 1% by weight with respect to the carboxylic acid, and more preferably 0.001 to 0.5% by weight. While the polymerization inhibitor may partially lose polymerization preventive effect by deterioration and the like, excessive amount of the polymerization inhibitor(s) is usually added in the reaction and distillation. So, most of them maintain polymerization preventive effect, and therefore recycling of the reaction liquid after evaporation of the hydroxyalkyl(meth)acrylate therefrom may also reduce the amount of polymerization inhibitor to be used.

The polymerization inhibitor may be directly added in the reactor or a distilling column, and may be successively or collectively supplied in a state beforehand dissolved in the reaction liquid, hydroxyalkyl(meth)acrylate, or the reaction liquid after evaporation of the hydroxyalkyl(meth)acrylate therefrom.

In order to further increase polymerization preventive effect in the producing process of the present invention, acids may also be used in combination with the polymerization inhibitor as is described in Japanese Patent Application Laid-Open No. 2003-267929.

In the producing process of the present invention, generally hydroxyalkyl(meth)acrylate as a targeted product is collected from the reaction liquid after termination of the reaction by evaporation (distillation refining). In detail, there may be adopted, but not limited to, processes of distillation using general-purpose distilling columns, or fractionating columns, such as packed columns, bubble tower and perforated plate tower, and the like. Other refining measures may also be used in combination with the distillation refining. As conditions of distillation refining, for example, the degree of vacuum is preferably 1 to 50 hPa, more preferably 1 to 20 hPa, and still more preferably 1 to 10 hPa. The distillation temperature is preferably 50 to 120 degrees C., and more preferably 60 to 100 degrees C. The distillation period of time is preferably 0.5 to 24 hours, more preferably 0.5 to 12 hours, still more preferably 1 to 6 hours, and especially preferably 1 to 3 hours. Since the reaction liquid after evaporation of the hydroxyalkyl(meth)acrylate therefrom may possibly give deterioration of properties of the reaction liquid, such as increase of viscosity, increase of by-products, and the like with thermal history by the temperature, or period of time, and the like, the reaction liquid concerned is preferably maintained at temperatures not more than the distillation temperature, and in a longer-term preservation in 5 days or more, it is preferably maintained at temperatures not more than 50 degrees C. In the case of distillation refining, the above-described polymerization inhibitor(s) may suitably be used.

When the amount of the catalyst used to the total amount of supplied (meth)acrylic acid is defined as a catalyst concentration in operation of the batch reaction in the producing process of the present invention, preferably adopted is a producing process, wherein the reaction is started in such a condition that the catalyst concentration exceeds 1, when the catalyst concentration represented with an amount of all used catalyst to a total amount of supply of (meth)acrylic acid is set as 1, (that is, set is a condition giving the catalyst concentration at the time of the reaction commencement exceeds 1). Adoption of this producing process can maintain the produced amount of hydroxyalkyl(meth)acrylate as a targeted product at almost the same level as a produced amount in conventional processes in a batch reaction system, and simultaneously may further suppress by-production of the biadduct of alkylene oxides that lowers product purity and presents adverse effects on quality.

Here, a point of time of reaction commencement is defined as a point of time wherein supply of (meth)acrylic acid as a raw material and, if needed, of alkylene oxide gives a reaction system temperature of not less than 40 degrees C., and a point of time of reaction of termination of the reaction is defined as a point of time wherein the acid component of the reaction liquid gives a concentration not more than 0.5% by weight. A catalyst concentration (for example, a catalyst concentration when the reaction is proceeding) after the reaction commencement is defined as a proportion of an amount of a sum total used of the catalyst supplied until the point of time to a total amount of (meth)acrylic acid supplied until any point of time during the above-mentioned reaction commencement and termination of the reaction. The reaction is preferably started under a condition giving a catalyst concentration exceeding 1, more preferably 1.1 to 20, and still more preferably 1.2 to 10. It is preferred that as long periods as possible may be maintained in a condition giving the catalyst concentration preferably exceeding 1.0 from the reaction commencement point of time to the reaction termination point of time. In detail, especially preferred is a setting of a condition of supply of raw material where supply of the total amount of the supply of (meth)acrylic acid ends after or at the same timing of the termination of supply of total amount of alkylene oxide to be supplied.

In the case of the batch reaction for the producing process of the present invention, preferably applicable is a producing process wherein a molar ratio of a total amount of alkylene oxide to a total amount of (meth)acrylic acid (alkylene oxide/(meth)acrylic acid) supplied to the reactor by the point of time is preferably controlled so as to give a value exceeding 1.0, during not less than 40% of supply period in all the supply periods wherein the temperature of supplied raw materials gives a temperature not less than 40 degrees C., in periods of time needed for supply of both raw materials. Adoption of this producing process can easily give hydroxyalkyl(meth)acrylate with a high quality, and realize both of a smaller content of alkyleneglycoldi(meth)acrylate and acid components in the batch reaction system.

All the supply periods wherein the temperature of supplied raw materials gives a temperature not less than 40 degrees C. in periods of time needed supply of the both raw materials represents, in other words, all the period needed for supply of alkylene oxide and/or (meth)acrylic acid in this reactor (the sum total period when there exist periods of concurrent supply of both alkylene oxide and (meth)acrylic acid and of supply of either of them) wherein the temperature of the raw materials (reaction liquid) supplied in the reactor by the point of time gives a temperature not less than 40 degrees C. Furthermore, in the case of supply, into the reactor, of raw materials warmed beforehand at a temperature not less than 40 degrees C., the period needed for supply of the materials is also included in all the supply period for the temperature of the supplied raw material to give a temperature not less than 40 degrees C.

In the case of adjustment so that the molar ratio (alkylene oxide/(meth)acrylic acid) may be in the above-described range, adjustment is performed so that all the supply periods where the temperature of the supplied raw materials gives a temperature not less than 40 degrees C. are preferably within not less than 60% of the supply periods in the periods needed for supply of the during all the supply times where the temperature of the supplied raw materials gives a temperature not less than 40 degrees C. Also in the case where the temperature of the raw materials supplied is less than 40 degrees C., adjustment is performed so that the molar ratio (alkylene oxide/(meth)acrylic acid) may be preferably in the range. In a more preferable embodiment, adjustment is performed so that the molar ratio (alkylene oxide/(meth)acrylic acid) may be within not less than 40% of all the supply periods where the temperature of supplied raw material gives temperature not less than 20 degrees C., preferably within not less than 60%, still more preferably within 100% of supply periods. In a most preferable embodiment, adjustment is performed so that the molar ratio (alkylene oxide/(meth)acrylic acid) may be in the range from a point of time of commencement of coexistence of catalyst, (meth)acrylic acid, and alkylene oxide in the reactor.

The method (order) of supply of (meth)acrylic acid and alkylene oxide as a raw material is not especially limited, as long as such a method of supply that the molar ratio (alkylene oxide/(meth)acrylic acid) exceeds 1.0 during a specific period mentioned above is adopted. In order to effectively suppress biadducts (furthermore, triadducts and the like), it is preferred that a part or whole amount of (meth)acrylic acid is supplied to the reactor by an initial supply and then alkylene oxide, or both alkylene oxide and the remainder of (meth)acrylic acid are supplied to the reactor. In the supply of the both raw materials, when there is included a phase where the molar ratio (alkylene oxide/(meth)acrylic acid) of the total amount of (meth)acrylic acid and the total amount of alkylene oxide already supplied in the reactor gives a value not more than 1.0, adjustment is preferably performed, within the above-mentioned phase, so that a sum total of the total amount of (meth)acrylic acid and the total amount of alkylene oxide already supplied in the reactor may be not more than 60% by weight with respect to a sum total of the total amount of supply of (meth)acrylic acid and the total amount of supply of alkylene oxide to be supplied by the time of termination of the reaction. Adjustment is more preferably performed so that a sum total of the total amount of (meth)acrylic acid and the total amount of alkylene oxide already supplied in the reactor may be not more than 50% by weight with respect to a sum total of the total amount of supply of (meth)acrylic acid and the total amount of supply of alkylene oxide to be supplied by the time of termination of the reaction. A phase where the molar ratio (alkylene oxide/(meth)acrylic acid) gives a value not more than 1.0 may relatively easily form a diester, adjustment of a total of the amount of supply of (meth)acrylic acid and alkylene oxide in the phase to the above-described range can suppress by-production of the diester still more effectively. When a total of the amount of supply of (meth)acrylic acid and alkylene oxide exceeds 60% by weight with respect to a sum total of the total amount of supply of (meth)acrylic acid and alkylene oxide, formation of the diester may not sufficiently be suppressed.

In the case of the batch reaction of the producing process of the present invention, there may be preferably applied a producing process of performing an operation for purge of a reactant gas containing alkylene oxide that exists in the reactor during the reaction. Application of this producing process can efficiently suppress by-production of alkyleneglycoldi(meth)acrylate and dialkylene glycol mono(meth)acrylate as impurities in the batch reaction system, and furthermore, the reactor does not need especially higher resistance to pressure. The measure of gas purge, for example, include a process for allowing stripping of alkylene oxide by purge of a reactant gas in the reactor to devices (for example, distilling column) maintained at a reduced pressure and the like.

The purge of the reactant gas may be suitably performed during the reaction, may preferably be carried out when a reaction conversion of all the supplied (meth)acrylic acid gives a value not less than 50%, and it is carried out when the reaction conversion of all the supplied (meth)acrylic acid more preferably gives a value not less than 90%, in order to efficiently suppress by-production of the diester and the biadduct. The purge of the reactant gas at a point of time of the reaction conversion of all the supplied (meth)acrylic acid giving less than 50% lowers the reaction yield, and simultaneously increases the remaining acid component. As a result, since this acid component is difficult to be removed by refining such as distillation and the like, there may arise possible decrease of purity of the product. In addition, in order to suppress a highest pressure applied to the reactor, and to perform the reaction with a reactor having lower resistance to pressure (for example, less than 1.0 MPa), the reactant gas may be purged at a point of time where an internal pressure exceeds 80%, and preferably 50%, of a resisting pressure limit of the reactor. The purge of the reactant gas may be continuously performed so as to give a fixed pressure, may be performed once, and may be separately performed in two or more steps.

The purge of the reactant gas including alkylene oxide existing in the reactor represents elimination, out of the reactor, of gas components (gas) existing in a gaseous phase in the reactor. Detailed operation techniques are not especially limited. For example, in the case of a reaction under application of pressure, release of the pressure in the reactor or pressure reduction in the reactor should just be carried out. When the reaction is not performed under application of a pressure, there may be performed flushing of the gaseous phase in the reactor by introduction of nitrogen gas or an inert gas (helium gas and the like) into the reactor, or pressure reduction in the reactor. Since a reaction under application of pressure is especially preferred, and an operation of purge of a reactant gas is a simpler process in the present invention, preferred are embodiments of the reaction under application of pressure and the purge of the reactant gas by release of a pressure in the reactor.

In the case of purge of the reactant gas, purge of all of the reactant gas in the reactor is not needed, purge of at least a part of the reactant gas existing in the reactor should just be performed based on kinds and a used proportion of raw materials, a resistance to pressure of the reactor used, a degree of completion of the reaction and the like. In detail, for example, in order to efficiently suppress by-production of the diester and the biadduct, it is preferred to determine the amount of gas purge so that an alkylene oxide gas concentration in the reactant gas existing in the reactor may give a concentration not more than 60% by volume, more preferably not less than 50% by volume, and still more preferably not more than 40% by volume. In order to suppress a highest pressure applied to a reactor low, and to perform the reaction in a reactor having lower resistance to pressure, it is preferable to determine an amount of gas purge so that an internal pressure of the reactor may give a pressure not more than 60% of an absolute pressure of the desired highest pressure, it is more preferable not more than 50%, and still more preferable not more than 40%.

A point of time of termination of the reaction (in other words, cooling commencement point of time of the reaction) should just be determined at a point of time of sufficient elimination of unreacted remaining (meth)acrylic acid. In detail, cooling is started, when the unreacted (meth)acrylic acid gives a value preferably not more than 0.2% by weight, and more preferably not more than 0.1% by weight. Commencement of cooling may be before or after purging of the reactant gas, and may be simultaneously performed. In the first process of the producing processes of the present invention as mentioned above, preferably maintained is a condition wherein the amount of the acid component to the amount of the catalyst in the reaction liquid gives a ratio calculatively not less than 0.010 and not more than 100 in terms of a molar ratio, and at the same time the reaction liquid after evaporation of hydroxyalkyl(meth)acrylate therefrom is used for the subsequent reaction.

In the first process, the condition is preferably maintained wherein the amount of the acid component in the reaction liquid gives a ratio calculatively not less than 0.010 and not more than 100 to the amount of the catalyst in the reaction liquid in terms of a molar ratio, as mentioned above, and the above-mentioned molar ratio is more preferably not less than 0.03 and not more than 50, and still more preferably not less than 0.05 and not more than 30. The above-mentioned molar ratio less than 0.010 inactivates the catalyst in the reaction liquid, and therefore use of the reaction liquid after evaporation of hydroxyalkyl(meth)acrylate therefrom to the subsequent reaction may not fully exhibit catalytic activity. In addition, the above-mentioned molar ratio exceeding 100 excessively raises an acid component concentration in the reaction liquid, and makes additional processes and the like needed for separation of the hydroxyalkyl(meth)acrylate and the acid component, leading to economical disadvantages. Here, the value of the above-mentioned molar ratio is same as a molar concentration (Mol %) ratio, i.e., a value of the ratio of a molar concentration (Mol %) of the acid component in the reaction liquid to a molar concentration (Mol %), of the catalyst in the reaction liquid.

The amount of the acid component in the reaction liquid includes, in detail, other acids, mentioned later, in addition to (meth)acrylic acid as a material compound. The operation of maintaining the above-mentioned molar ratio in the reaction liquid represents an operation wherein the molar ratio is maintained, in all the period (hereinafter, referred to as a maintenance period), at least from a point of time of supply of the catalyst into the reaction liquid, until an actual start of a next reaction by use of the reaction liquid after the evaporation of hydroxyalkyl (meth)acrylate therefrom to the subsequent reaction. Accordingly, the molar ratio always needs to be maintained not only during the reaction, but in cooling in the end of the reaction, in a standby period until evaporation of the targeted product, and in and after evaporation of the targeted product.

Here, for the amount in the reaction liquid catalyst, the above described expression of "calculatively" represents an amount of the catalyst existing in the reaction liquid at any point of time within the above-mentioned maintenance period. In detail, in the case of a batch reaction, the expression represents a total amount of the catalyst supplied into the reaction liquid up to a certain point of time, and in a successive reaction, it represents an amount converted from a catalyst concentration in a reaction liquid in a reactor at a certain point of time (a point of time of being taken out from the reactor in a reaction liquid after being taken out from the reactor). In addition, calculation of the amount of catalysts in the reaction liquid is performed without taking into consideration the drop or loss of original catalytic capability by being used for the reaction. On the other hand, the amount of the acid component in the reaction liquid represents an amount of the acid components, such as (meth)acrylic acid, that exist in the reaction liquid in the reactor at any point of time. Since (meth)acrylic acid is a material compound of this reaction, it is necessary to be taken into consideration that the (meth)acrylic acid is consumed with progress of a reaction, and in detail, the amount of the acid components represents a value obtained from a measured value in such a manner that a neutralization titration is performed by sampling a part of the reaction liquid at a predetermined point of time to calculate a concentration of the acid component in this reaction liquid.

Means of maintaining the above-mentioned molar ratio in the reaction liquid are not limited in the first process, and, for example, preferably include:
(i) a means of for sufficiently supplying the amount of the (meth)acrylic acid as a material compound into the reaction liquid to such an extent that the molar ratio may be maintained;
(ii) a means of supplying other acids, such as acids having reactivity lower than that of the (meth)acrylic acid as a material compound, into the reaction liquid;

(iii) a means of removing unreacted alkylene oxide from the reaction liquid simultaneously at the end of the reaction (for example, a gas purge, a diffusion, and the like);

(iv) a means of setting the reaction temperature immediately before the end of the reaction not less than 5 degrees C. lower than a preset temperature, or for setting a cooling time at the end of the reaction shorter and the like. Supply in the measures of the above-mentioned (i) or (ii) may be gradually performed by management of an amount of the acid component in the reaction liquid accompanying progress of the reaction.

The above-mentioned acids having low reactivity include, for example, carboxylic acids having not less than six of carbon numbers, and saturated carboxylic acids and the like such as octanoic acid, iso-octanoic acid, decanoic acid, and dodecanoic acid. The first process is applicable to all the well-known or already proposed producing processes of hydroxyalkyl(meth)acrylate by a reaction of (meth)acrylic acid and alkylene oxide. For example, it may preferably be applied for a producing process wherein the molar ratio of alkylene oxide to (meth)acrylic acid initially supplied gives a ratio not less than 1. When the above-mentioned molar ratio initially supplied gives a ratio not less than 1.4 in this producing process, a problem of significant inactivation of a catalyst has been induced. However, when the molar ratio of the amount of the acid component to the amount of the catalyst in the reaction liquid is maintained by application of the first process so that the above-mentioned range may be satisfied, the above-mentioned problem may easily be solved. The reason is that a large molar ratio at the time of the above-mentioned initial supply might make the molar ratio of the amount of an acid component to the amount of the catalyst in the reaction liquid smaller than the molar ratio of the first process during the reaction.

In the first process, a reaction liquid after evaporation of the hydroxyalkyl(meth)acrylate as a targeted product therefrom is used for the subsequent reaction, and a catalyst once used for the reaction is again used for a same reaction (recycling). The reaction liquid after evaporation is not limited, there may be used a reaction liquid with the above-mentioned evaporation performed thereto after a perfect reaction of the (meth)acrylic acid as a material compound and alkylene oxide, or a reaction liquid after the above-mentioned evaporation performed thereto after termination of the reaction in a predetermined stage during the reaction of (meth)acrylic acid and alkylene oxide. The reaction liquid concerned may be selected with suitable consideration for further improved efficiency of recycling of the catalyst, of a yield of a targeted product, and the like.

In addition, in the reaction liquid after the evaporation, the hydroxyalkyl(meth)acrylate as a targeted product may completely be evaporated off, and may partially remain without evaporation, and existence of this substance is not limited. In addition, other components, such as various by-products and material compounds, are not limited, either, and these may remain in the reaction liquid after the evaporation, and may be evaporated off with the targeted product. For example, when the reaction liquid is used for the subsequent reaction with the remaining biadduct (dialkylene glycol mono(meth)acrylate) of the alkylene oxide as a by-product, the by-production of this biadduct can effectively be suppressed in the subsequent reaction. Although the whole amount of the reaction liquid after the evaporation is preferably used for the subsequent reaction in the first process, only a part may be used or the reaction liquid may be separately used for two or more reactions, and the method of use is not limited.

In the second process in the producing processes of the present invention, as described above, it is important that supply of a dialkylene glycol mono(meth)acrylate into a reaction system causes coexistence of the dialkylene glycol mono (meth)acrylate (biadduct) in a reaction liquid. In the second process, preferably an amount of the above-mentioned biadduct coexisting is calculatively 2 to 100 in terms of a molar ratio to an amount of the catalyst in the reaction liquid, more preferably 5 to 80, still more preferably 5 to 60, and especially preferably 5 to 40. The molar ratio less than 2 may not give suppressing effect of the biadduct. The molar ratio exceeding 100 exhibits the suppressing effect of the biadduct, it may possibly increase an absolute amount of the biadduct in the reaction liquid, and may lower a yield and purity.

Here, the expression "calculatively" represents, in the amount of the catalyst in the reaction liquid, an amount of the catalyst existing in the reaction liquid at a predetermined point of time before the reaction or during the reaction. In detail, in a batch reaction, the expression represents a total amount of the catalyst supplied in the reaction liquid by a certain point of time. In a successive reaction, the expression represents an amount converted from the catalyst concentration in the reaction liquid in the reactor at a certain point of time. In addition, calculation of the amount of the catalyst in the reaction liquid is performed without taking into consideration the drop or loss of original catalytic capability by being used for the reaction.

In the second process, modes for supplying of dialkylene glycol mono(meth)acrylate in a reaction system is not especially limited. For example, dialkylene glycol mono(meth) acrylate may be supplied before the reaction of (meth)acrylic acid and alkylene oxide, dialkylene glycol mono(meth)acrylate may be supplied during the reaction of (meth)acrylic acid and alkylene oxide in the reaction liquid, and dialkylene glycol mono(meth)acrylate are preferably beforehand supplied before the reaction of (meth)acrylic acid and alkylene oxide. Thus, the beforehand supply before the reaction exhibits still higher suppressing effect of formation of the above-mentioned biadduct. In addition, in supply of the beforehand biadduct before the reaction, a whole amount may be supplied and a part may be supplied (in the partial supply, the remainder is supplied during the reaction in the reaction liquid), the supply mode being not limited, and a larger amount of supply is preferable, and a whole amount of supply is still more preferable.

In the second process, a source of the biadduct supplied in a reaction system is not limited. In general, it is the reaction liquid after the evaporation of the hydroxyalkyl(meth)acrylate as a targeted product therefrom in this reaction performed previously, and the reaction liquid including the biadduct formed in the previous reaction is preferably used. That is, the dialkylene glycol mono(meth)acrylate included in the reaction liquid after evaporation of the hydroxyalkyl(meth)acrylate therefrom is preferably used for supply into the reaction system. This mode can effectively reuse the residual reaction liquid. Since the catalyst once used for the reaction is also included in this residual reaction liquid, the catalyst may preferably be again used (recycling) for the same reaction.

As the reaction liquid after the evaporation, may be used a reaction liquid with the evaporation performed thereto after a perfect reaction between (meth)acrylic acid and alkylene oxide as material compounds in the previous reaction, and may also be used a reaction liquid with the evaporation performed thereto after termination of the reaction at the predetermined stage during the reaction between (meth)acrylic acid and alkylene oxide, thus the reaction liquid to be used being not limited. The reaction liquid concerned may be selected with suitable consideration of further improved efficiency of recycling of the catalyst, of a yield of a targeted product, and the like. In addition, hydroxyalkyl(meth)acrylate as a targeted product may be completely evaporated from the reaction liquid after the above-mentioned evaporation, it may partially remain without complete evaporation, and thus carrying out of evaporation is not limited.

The whole amount of the reaction liquid after the evaporation of the targeted product therefrom is preferably used for the subsequent reaction in the second process, only a part may be used or the reaction liquid may be separately used for two or more reactions, and the method of use is not limited. In the second process, the above-described first process in the producing processes of the present invention mentioned above is preferably applicable. The detailed mode of the first process has previously been described.

In the second process, for example, there is preferably applied a producing process that the molar ratio of the alkylene oxide to the (meth)acrylic acid initially supplied gives a ratio not less than 1. In this producing process, a problem of remarkable inactivation of the catalyst has been induced when the molar ratio in the initial supply gives a ratio, for example, not less than 1.4. However, maintenance for satisfying a range of the molar ratio of the amount of the acid component to the amount of the catalyst in the reaction liquid can easily solve the above-mentioned problem by application of the first process. The reason is probably that a large molar ratio at the time of the initial supply may once give less molar ratio of the amount of the acid component to the amount of the catalyst in the reaction liquid than the molar ratio defined by the first process during the reaction.

In the second process, preferably used is a producing process using the reaction liquid containing a novel catalyst additionally supplied after the evaporation of hydroxyalkyl (meth)acrylate therefrom for the subsequent reaction. In detail, in this producing process, the used catalyst is collected in a state of a solution after evaporation of the targeted product from the reaction liquid, and a novel catalyst is additionally supplied to the recovered liquid to be reused for the subsequent reaction. Application of this producing process greatly reduces an amount of the catalyst to be used, and realizes lower costs, outstanding economical efficiency, and simpler operation allowing reuse of the catalyst. Furthermore this application can secure a higher catalyst recovery rate, and sufficient catalyst reaction efficiency.

In use for a subsequent reaction of a catalyst including the catalyst in the reaction liquid containing the catalyst used for the reaction after evaporation of the targeted product therefrom (hereinafter, referred to as a residual reaction liquid), and a catalyst to be newly added (hereinafter, referred to as a novel catalyst), modes for adding of the novel catalyst to the residual reaction liquid include, for example: a mode wherein the novel catalyst is beforehand dissolved in the residual reaction liquid and then the catalyst is used for a subsequent reaction; a mode wherein after commencement of the subsequent reaction, the novel catalyst is dissolved in the residual reaction liquid; a mode wherein a part of the novel catalyst is beforehand dissolved in the residual reaction liquid, and then a remaining novel catalyst is dissolved after commencement of the subsequent reaction; and a mode wherein the novel catalyst is beforehand dissolved in a part of the residual reaction liquid, and then a remaining residual reaction liquid is added after commencement of the subsequent reaction, and the modes of addition are not especially limited to these modes. Especially, it is preferable that all of the novel catalyst to be added is dissolved beforehand in a whole amount of the residual reaction liquid to be used for a subsequent reaction and then an obtained reaction liquid is used for the subsequent reaction, because of easy handling as a catalyst to be used for the subsequent reaction, and of avoidance of complicated operation.

It is preferred that the novel catalyst is an identical catalyst that can be used for the producing process of the present invention illustrated above. The residual reaction liquid is a liquid after evaporation of the hydroxyalkyl(meth)acrylate as a targeted product from the liquid after the reaction, but the targeted product need not to be completely evaporated off, allowing a certain amount remained. The whole amount of the residual reaction liquid may be used for the subsequent reaction, only a part may be used, and the residual reaction liquid may optionally be divided to be used for two or more reactions. At this time, a mode of use is not limited as long as at least a part of the catalyst once used for the reaction is again used as a reaction catalyst. In detail, for example, a mode may be mentioned wherein a part of the residual reaction liquid, preferably 20 to 90% by weight, more preferably 30 to 80% by weight, still more preferably 40 to 80% by weight, especially preferably 50 to 80% by weight, is recycled for the subsequent reaction system, and the remainder of the residual reaction liquid is disposed.

In the case where the whole amount of the residual reaction liquid is used for the subsequent reaction, 100% by weight of the catalyst necessary for the reaction system is preferably additionally supplied, when the catalyst in the residual reaction liquid to be recycled is completely deactivated. When the catalyst in the residual reaction liquid to be recycled is not deactivated, and can cover 100% by weight of the amount of the catalyst necessary for the reaction system, the additional supply is unnecessary. When a part of the residual reaction liquid is used for the subsequent reaction and the remainder is disposed, an amount of the catalyst included in the disposed residual reaction liquid is preferably supplied. When a part of the catalyst included in a part of the residual reaction liquid is deactivated, preferably is supplied a total amount of an amount corresponding to a deactivated catalyst, and an amount of the catalyst included in the disposed residual reaction liquid.

EXAMPLE

Detailed descriptions of the present invention will, hereinafter, be given with reference to Examples and Comparative examples, but the present invention is not limited to them. Hereinafter, "part by weight" is only referred to as "part," and "liter" is only with "L." In addition, "% by weight" may be referred to as "wt %."

Example 1-1

Fresh Reaction

A part of 140 g in a total amount of supply of 420 g of acrylic acid, chromium acetate 2.52 g (0.010 mol) as a catalyst, phenothiazine 0.42 g as a polymerization inhibitor were introduced into an autoclave of volume 1 L made of SUS316 with a stirrer. The interior of the autoclave was replaced with nitrogen gas, subsequently, the temperature was raised up to 85 degrees C., and the internal pressure was adjusted to 0.05 MPa (G). Ethyleneoxide was supplied at 136 g/h for 0.7 hour (94 g), then acrylic acid at 215 g/h (280 g), and ethyleneoxide at 136 g/h (178 g) were supplied for 1.3 hours, and the temperature of 85 degrees C. was maintained in the meantime, and the reaction was performed. The reaction temperature after termination of supply of acrylic acid and ethyleneoxide was maintained constant at 85 degrees C., and the reaction was continued until the concentration (measurement by neutralization titration) of the acid component as acrylic acid gave 0.10 wt %. Since the concentration of the acid component after continuation of the reaction of 1.0 hours gave 0.10 wt %, the reaction liquid was cooled to a temperature not more than 30 degrees C. in 10 minutes (the reaction continuation period eventually gave 1.2 hours). The acid component of the obtained reaction liquid gave 0.05 wt % (the molar ratio of the acid component to the catalyst: 0.07).

Subsequently, a glass round bottom flask of a volume of 1 L fitted in a vacuum distillation unit was decompressed to a degree of vacuum of 4 hPa, and the reaction liquid obtained above was transported to the flask by compression transportation from the autoclave. Unreacted ethyleneoxide was diffused for 30 minutes at an internal temperature of 40 to 50 degrees C., while bubbling of air was carried out at 3 mL/min. The acid component of the obtained reaction liquid gave 0.05 wt % (molar ratio of the acid component to the catalyst: 0.07). Then, the obtained reaction liquid was refined by distillation for 3 hours at an internal temperature of 50 to 90 degrees C., and 69.5 g of a reaction liquid after evaporation of the hydroxyethyl acrylate therefrom was obtained. The acid component of the obtained reaction liquid gave 0.05 wt % (molar ratio of the acid component to the catalyst: 0.07).

<Recycling Reaction>

The reaction liquid after evaporation of hydroxyethyl acrylate therefrom 69.5 g, and a part of 70.5 g in a total amount of supply of 380 g of acrylic acid were introduced into an autoclave of a volume of 1 L made of SUS316 with a stirrer. The interior of the autoclave was replaced with nitrogen gas, subsequently, the temperature was raised up to 85 degrees C., and the internal pressure was adjusted to 0.05 MPa (G). Ethyleneoxide was supplied at 123 g/h for 0.4 hour (47.5 g), then acrylic acid at 193.5 g/h (309.5 g), and ethyleneoxide at 123 g/h (198.5 g) were supplied for 1.6 hours, and a temperature of 85 degrees C. was maintained in the meantime, and the reaction was performed. The reaction temperature after termination of supply of acrylic acid and ethyleneoxide was maintained constant at 85 degrees C., and the reaction was continued until the concentration (measurement by neutralization titration) of the acid component as acrylic acid gave 0.10 wt %. Then the concentration of the acid component after continuation of the reaction of 1.3 hours gave 0.10 wt %.

Example 1-2

Fresh Reaction

A same operation as in Example 1-1 was performed except that octanoic acid 0.5 g was introduced into a glass round bottom flask with a volume of 1 L set in a vacuum distillation unit, the glass round bottom flask was decompressed in a degree of vacuum of 4 hPa, and the obtained reaction liquid was transported to the flask by compression transportation from the autoclave. In a same manner as in Example 1-1, while bubbling of air was carried out at 3 mL/min, unreacted ethyleneoxide was diffused for 30 minutes at the internal temperature of 40 to 50 degrees C. The acid component of the obtained reaction liquid gave 0.06 wt % (the molar ratio of the acid component to the catalyst: 0.08). Then, the obtained reaction liquid was refined by distillation for 3 hours at an internal temperature of 50 to 90 degrees C., and 69.5 g of a reaction liquid after evaporation of the hydroxyethyl acrylate therefrom was obtained. The acid component of the obtained reaction liquid gave 0.06 wt % (molar ratio of the acid component to the catalyst: 0.08).

<Recycling Reaction>

The reaction liquid after evaporation of hydroxyethyl acrylate therefrom 69.5 g, a part of 70.5 g in a total amount of supply of acrylic acid of 380 g were introduced into an autoclave of volume of 1 L made of SUS316 with a stirrer. The interior of the autoclave was replaced with nitrogen gas, subsequently, the temperature was raised up to 85 degrees C., and the internal pressure was adjusted to 0.05 MPa (G). Ethyleneoxide was supplied at 123 g/h for 0.4 hour (47.5 g), then acrylic acid at 193.5 g/h (309.5 g), and ethyleneoxide at 123 g/h (198.5 g) were supplied for 1.6 hours, and a temperature of 85 degrees C. was maintained in the meantime, and the reaction was performed. The reaction temperature after termination of supply of acrylic acid and ethyleneoxide was maintained constant at 85 degrees C., and the reaction was continued until the concentration (measurement by neutralization titration) of the acid component as acrylic acid gave 0.10 wt %. Then the concentration of the acid component after continuation of the reaction for 1.0 hours gave 0.10 wt %.

Comparative Example 1-1

Fresh Reaction

A part of 137 g in a total amount of supply of 411 g of acrylic acid, chromium acetate 2.52 g (0.010 mol) as a catalyst, phenothiazine 0.42 g as a polymerization inhibitor were introduced into an autoclave of volume of 1 L made of SUS316 with a stirrer. The interior of the autoclave was replaced with nitrogen gas, subsequently, the temperature was raised up to 85 degrees C., and the internal pressure was adjusted to 0.05 MPa (G). Ethyleneoxide was supplied at 136 g/h for 0.7 hour (94 g), then acrylic acid at 211 g/h (274 g), and ethyleneoxide at 136 g/h (178 g) were supplied for 1.3 hours, and a temperature of 85 degrees C. was maintained in the meantime, and the reaction was performed. The reaction temperature after termination of supply of acrylic acid and ethyleneoxide was maintained constant at 85 degrees C., and the reaction was continued until the concentration (measurement by neutralization titration) of the acid component as acrylic acid gave 0.10 wt %. Since the concentration of the acid component after continuation of the reaction for 0.85 hours gave 0.10 wt %, the reaction liquid was cooled to a temperature not more than 30 degrees C. in 30 minutes (the reaction continuation period eventually gave 1.05 hours). The acid component of the obtained reaction liquid gave 0.005 wt % (the molar ratio of the acid component to the catalyst: 0.007).

Subsequently, the obtained reaction liquid was transported by compression transportation to a glass round bottom flask of volume of 1 L fitted in a vacuum distillation unit. Unreacted ethyleneoxide was diffused for 30 minutes at an internal temperature of 40 to 50 degrees C. at a degree of vacuum of 4 hPa, while bubbling of air was carried out at 3 mL/min. The acid component of the obtained reaction liquid gave 0.005 wt % (molar ratio of the acid component to the catalyst: 0.007). Then, the obtained reaction liquid was refined by distillation for 3 hours at an internal temperature of 50 to 90 degrees C., and 69.5 g of a reaction liquid after evaporation of the hydroxyethyl acrylate therefrom was obtained. The acid component of the obtained reaction liquid gave 0.005 wt % (molar ratio of the acid component to the catalyst: 0.007).

<Recycling Reaction>

The reaction liquid after evaporation of hydroxyethyl acrylate therefrom 69.5 g, and a part of 70.5 g in a total amount of supply of 380 g of acrylic acid were introduced into an autoclave of a volume of 1 L made of SUS316 with a stirrer. The interior of the autoclave was replaced with nitrogen gas, subsequently, the temperature was raised up to 85 degrees C., and the internal pressure was adjusted to 0.05 MPa (G). Ethyleneoxide was supplied at 123 g/h for 0.4 hour (47.5 g), then acrylic acid at 193.5 g/h (309.5 g), and ethyleneoxide at 123 g/h (198.5 g) were supplied for 1.6 hours, and a temperature of 85 degrees C. was maintained in the meantime, and the reaction was performed. The reaction temperature after termination of supply of acrylic acid and ethyleneoxide was maintained constant at 85 degrees C. Although the reaction was continued until the concentration of the acid component as acrylic acid gave 0.10 wt % (measurement by neutralization titration), the concentration of the acid component gave 42 wt % even after continuation of the reaction for 1.3 hours.

Since the concentration of the acid component in the reaction liquid was high, even in the same reaction period as in Example 1-1, it could be determined that the catalyst was inactivated.

Example 1-3

Fresh Reaction

A part of 127 g in a total amount of supply of 380 g of acrylic acid, chromium acetate 2.28 g (0.009 mol) as a catalyst, hydroquinone monomethyl ether 0.38 g as a polymerization inhibitor were introduced into an autoclave of volume 1 L made of SUS316 with a stirrer. The interior of the autoclave was replaced with nitrogen gas, subsequently, the temperature was raised up to 85 degrees C., and the internal pressure was adjusted to 0.05 MPa (G). Propyleneoxide was supplied at 158 g/h for 0.7 hour (113 g), then acrylic acid at 196 g/h (235 g), and propyleneoxide at 158 g/h (202 g) were supplied for 1.3 hours, and a temperature of 85 degrees C. was maintained in the meantime, and the reaction was performed. The reaction temperature after termination of supply of acrylic acid and propyleneoxide was maintained constant at 85 degrees C., and the reaction was continued until the concentration of the acid component as acrylic acid gave 0.10 wt % (measurement by neutralization titration). Since the concentration of the acid component after continuation of the reaction of 1.5 hours gave 0.10 wt %, the reaction liquid was cooled to a temperature not more than 30 degrees C. in 10 minutes (the reaction continuation period eventually gave 1.7 hours). The acid component of the obtained reaction liquid gave 0.04 wt % (the molar ratio of the acid component to the catalyst: 0.06).

Subsequently, a glass round bottom flask of a volume of 1 L fitted in a vacuum distillation unit was decompressed to a degree of vacuum of 4 hPa, and the reaction liquid obtained above was transported to the flask by compression transportation from the autoclave. Unreacted propylene oxide was diffused for 30 minutes at an internal temperature of 40 to 50 degrees C., while bubbling of air was carried out at 3 mL/min. The acid component of the obtained reaction liquid gave 0.04 wt % (the molar ratio of the acid component to the catalyst: 0.06). Then, the obtained reaction liquid was refined by distillation for 3 hours at an internal temperature of 50 to 90 degrees C., and 69.5 g of a reaction liquid after evaporation of the hydroxypropyl acrylate therefrom was obtained. The acid component of the obtained reaction liquid gave 0.04 wt % (the molar ratio of the acid component to the catalyst: 0.06).
<Recycling Reaction 1>

The reaction liquid after evaporation of hydroxypropyl acrylate therefrom 69.5 g, and a part of 57.5 g in a total amount of supply of 342 g of acrylic acid were introduced into an autoclave of a volume of 1 L made of SUS316 with a stirrer. The interior of the autoclave was replaced with nitrogen gas, subsequently, the temperature was raised up to 85 degrees C., and the internal pressure was adjusted to 0.05 MPa (G). Propyleneoxide was supplied at 142 g/h for 0.4 hour (51 g), then acrylic acid at 173.5 g/h (284.5 g), and propyleneoxide at 142 g/h (232.5 g) were supplied for 1.6 hours, and a temperature of 85 degrees C. was maintained in the meantime, and the reaction was performed. The reaction temperature after termination of supply of acrylic acid and propyleneoxide was maintained constant at 85 degrees C., and the reaction was continued until the concentration (measurement by neutralization titration) of the acid component as acrylic acid gave 0.10 wt %. Since the concentration of the acid component after continuation of the reaction of 1.5 hours gave 0.10 wt %, the reaction liquid was cooled to a temperature not more than 30 degrees C. in 10 minutes (the reaction continuation period eventually gave 1.7 hours). The acid component of the obtained reaction liquid gave 0.04 wt % (molar ratio of the acid component to the catalyst: 0.06). Subsequently, a glass round bottom flask of a volume of 1 L fitted in a vacuum distillation unit was decompressed to a degree of vacuum of 4 hPa, and the reaction liquid obtained above was transported to the flask by compression transportation from the autoclave. Unreacted propyleneoxide was diffused for 30 minutes at an internal temperature of 40 to 50 degrees C., while bubbling of air was carried out at 3 mL/min. The acid component of the obtained reaction liquid gave 0.04 wt % (the molar ratio of the acid component to the catalyst: 0.06). Then, the obtained reaction liquid was refined by distillation for 3 hours at an internal temperature of 50 to 90 degrees C., and 69.5 g of a reaction liquid after evaporation of the hydroxypropyl acrylate therefrom was obtained. The acid component of the obtained reaction liquid gave 0.04 wt % (the molar ratio of the acid component to the catalyst: 0.06).
<Recycling Reaction 2>

The reaction liquid after evaporation of hydroxypropyl acrylate therefrom 69.5 g, and a part of 57.5 g in a total amount of supply of 342 g of acrylic acid were introduced into an autoclave of a volume of 1 L made of SUS316 with a stirrer. The interior of the autoclave was replaced with nitrogen gas, subsequently, the temperature was raised up to 85 degrees C., and the internal pressure was adjusted to 0.05 MPa (G). Propyleneoxide was supplied at 142 g/h for 0.4 hour (51 g), then acrylic acid at 173.5 g/h (284.5 g), and propyleneoxide at 142 g/h (232.5 g) were supplied for 1.6 hours, and a temperature of 85 degrees C. was maintained in the meantime, and the reaction was performed. The reaction temperature after termination of supply of acrylic acid and propyleneoxide was maintained constant at 85 degrees C., and the reaction was continued until the concentration (measurement by neutralization titration) of the acid component as acrylic acid gave 0.10 wt %. Then the concentration of the acid component after continuation of the reaction of 1.5 hours gave 0.10 wt %.

Comparative Example 1-2

Fresh Reaction

A part of 127 g in a total amount of supply of 380 g of acrylic acid, chromium acetate 2.28 g (0.009 mol) as a catalyst, hydroquinone monomethyl ether 0.38 g as a polymerization inhibitor were introduced into an autoclave of a volume 1 L made of SUS316 with a stirrer. The interior of the autoclave was replaced with nitrogen gas, subsequently, the temperature was raised up to 85 degrees C., and the internal pressure was adjusted to 0.05 MPa (G). Propyleneoxide was supplied by 161 g/h for 0.7 hour (113 g), then acrylic acid by 196 g/h (253 g), and propyleneoxide by 161 g/h (208 g) were supplied for 1.3 hours, and a temperature of 85 degrees C. was maintained in the meantime, and the reaction was performed. The reaction temperature after termination of supply of acrylic acid and propyleneoxide was maintained constant at 85 degrees C., and the reaction was continued until the concentration (measurement by neutralization titration) of the acid component as acrylic acid gave 0.10 wt %. Then the concentration of the acid component after continuation of the reaction of 1.4 hours gave 0.10 wt %. The reaction liquid was cooled to a temperature not more than 30 degrees C. in 30 minutes (the reaction continuation period eventually gave 1.6 hours). The acid component of the obtained reaction liquid gave 0.005 wt % (molar ratio of the acid component to the catalyst: 0.008).

Subsequently, a glass round bottom flask of a volume of 1 L fitted in a vacuum distillation unit was decompressed to a degree of vacuum of 4 hPa, and the reaction liquid obtained above was transported to the flask by compression transportation from the autoclave. Unreacted propylentoxide was diffused for 30 minutes at an internal temperature of 40 to 50 degrees C., while bubbling of air was carried out at 3 mL/min. The acid component of the obtained reaction liquid gave 0.005 wt % (molar ratio of the acid component to the catalyst: 0.008). Then, the obtained reaction liquid was refined by distillation for 3 hours at an internal temperature of 50 to 90 degrees C., and 69.5 g of a reaction liquid after evaporation of the hydroxypropyl acrylate therefrom was obtained. The acid component of the obtained reaction liquid gave 0.005 wt % (molar ratio of the acid component to the catalyst: 0.008).

<Recycling Reaction 1>

The reaction liquid after evaporation of hydroxypropyl acrylate therefrom 69.5 g, and a part of 57.5 g in a total amount of supply of 342 g of acrylic acid were introduced into an autoclave of a volume of 1 L made of SUS316 with a stirrer. The interior of the autoclave was replaced with nitrogen gas, subsequently, the temperature was raised up to 85 degrees C., and the internal pressure was adjusted to 0.05 MPa (G). Propyleneoxide was supplied at 145 g/h for 0.4 hour (51 g), then acrylic acid at 173.5 g/h (284.5 g), and propyleneoxide at 145 g/h (238 g) were supplied for 1.6 hours, and a temperature of 85 degrees C. was maintained in the meantime, and the reaction was performed. The reaction temperature after termination of supply of acrylic acid and propyleneoxide was maintained constant at 85 degrees C., and the reaction was continued until the concentration (measurement by neutralization titration) of the acid component as acrylic acid gave 0.10 wt %. Then the concentration of the acid component after continuation of the reaction of 1.5 hours gave 0.10 wt %. The reaction liquid was cooled to a temperature not more than 30 degrees C. in 30 minutes (the reaction continuation period eventually gave 1.7 hours). The acid component of the obtained reaction liquid gave 0.005 wt % (molar ratio of the acid component to the catalyst: 0.008).

Subsequently, a glass round bottom flask of a volume of 1 L fitted in a vacuum distillation unit was decompressed to a degree of vacuum of 4 hPa, and the reaction liquid obtained above was transported to the flask by compression transportation from the autoclave. Unreacted propyleneoxide was diffused for 30 minutes at an internal temperature of 40 to 50 degrees C., while bubbling of air was carried out at 3 mL/min. The acid component of the obtained reaction liquid gave 0.005 wt % (molar ratio of the acid component to the catalyst: 0.008). Then, the obtained reaction liquid was refined by distillation for 3 hours at an internal temperature of 50 to 90 degrees C., and 69.5 g of a reaction liquid after evaporation of the hydroxypropyl acrylate therefrom was obtained. The acid component of the obtained reaction liquid gave 0.005 wt % (molar ratio of the acid component to the catalyst: 0.008).

<Recycling Reaction 2>

The reaction liquid after evaporation of hydroxypropyl acrylate therefrom 69.5 g, and a part of 57.5 g in a total amount of supply of 342 g of acrylic acid were introduced into an autoclave of a volume of 1 L made of SUS316 with a stirrer. The interior of the autoclave was replaced with nitrogen gas, subsequently, the temperature was raised up to 85 degrees C., and the internal pressure was adjusted to 0.05 MPa (G). Propyleneoxide was supplied at 142 g/h for 0.4 hour (51 g), then acrylic acid at 173.5 g/h (284.5 g), and propyleneoxide at 142 g/h (232.5 g) were supplied for 1.6 hours, and a temperature of 85 degrees C. was maintained in the meantime, and the reaction was performed. The reaction temperature after termination of supply of acrylic acid and propyleneoxide was maintained constant at 85 degrees C., and the reaction was continued until the concentration of the acid component as acrylic acid gave 0.10 wt % (measurement by neutralization titration). Then the concentration of the acid component after continuation of the reaction of 1.7 hours gave 0.10 wt %.

As compared with Example 1-3, a gradually prolonged period of time until a concentration of the acid component gives 0.10 wt % shows a tendency of decrease of catalytic activity.

Example 1-4

Fresh Reaction

A part of 137 g in a total amount of supply of 410 g of methacrylic acid, chromium acetate 2.46 g (0.010 mol) as a catalyst, hydroquinone monomethyl ether 0.41 g as a polymerization inhibitor were introduced into an autoclave of a volume 1 L made of SUS316 with a stirrer. The interior of the autoclave was replaced with nitrogen gas, subsequently, the temperature was raised up to 85 degrees C., and the internal pressure was adjusted to 0.05 MPa (G). Propyleneoxide was supplied at 143 g/h for 0.7 hour (102 g), then methacrylic acid at 212 g/h (273 g), and propyleneoxide at 143 g/h (183 g) were supplied for 1.3 hours, and a temperature of 85 degrees C. was maintained in the meantime, and the reaction was performed. The reaction temperature after termination of supply of methacrylic acid and propyleneoxide was maintained constant at 85 degrees C., and the reaction was continued until the concentration of the acid component as methacrylic acid gave 0.10 wt % (measurement by neutralization titration). Then the concentration of the acid component after continuation of the reaction of 1.6 hours gave 0.10 wt %. The reaction liquid was cooled to a temperature not more than 30 degrees C. in 10 minutes (the reaction continuation period eventually gave 1.8 hours). The acid component of the obtained reaction liquid gave 0.03 wt % (molar ratio of the acid component to the catalyst: 0.03).

Subsequently, a glass round bottom flask of a volume of 1 L fitted in a vacuum distillation unit was decompressed to a degree of vacuum of 4 hPa, and the reaction liquid obtained above was transported to the flask by compression transportation from the autoclave. Unreacted propyleneoxide was diffused for 30 minutes at an internal temperature of 40 to 50 degrees C., while bubbling of air was carried out at 3 mL/min. The acid component of the obtained reaction liquid gave 0.03 wt % (molar ratio of the acid component to the catalyst: 0.03). Then, the obtained reaction liquid was refined by distillation for 3 hours at an internal temperature of 50 to 90 degrees C., and 69.5 g of a reaction liquid after evaporation of the hydroxypropyl methacrylate therefrom was obtained. The acid component of the obtained reaction liquid gave 0.03 wt % (molar ratio of the acid component to the catalyst: 0.03).

<Recycling Reaction 1>

The reaction liquid after evaporation of hydroxypropyl methacrylate therefrom 69.5 g, and a part of 67.5 g in a total amount of supply of 369 g of methacrylic acid were introduced into an autoclave of a volume of 1 L made of SUS316 with a stirrer. The interior of the autoclave was replaced with nitrogen gas, subsequently, the temperature was raised up to 85 degrees C., and the internal pressure was adjusted to 0.05 MPa (G). Propyleneoxide was supplied by 128 g/h for 0.4 hour (50 g), then methacrylic acid by 187.5 g/h (301.5 g), and propyleneoxide by 128 g/h (206 g) were supplied for 1.6 hours, and a temperature of 85 degrees C. was maintained in the meantime, and the reaction was performed. The reaction temperature after termination of supply of methacrylic acid and propyleneoxide was maintained constant at 85 degrees C., and the reaction was continued until the concentration of the acid component as methacrylic acid gave 0.10 wt % (measurement by neutralization titration). Then the concentration of the acid component after continuation of the reaction of 1.6 hours gave 0.10 wt %. The reaction liquid was cooled to a temperature not more than 30 degrees C. in 10 minutes (the reaction continuation period eventually gave 1.8 hours). The acid component of the obtained reaction liquid gave 0.03 wt % (molar ratio of the acid component to the catalyst: 0.03).

Subsequently, a glass round bottom flask of a volume of 1 L fitted in a vacuum distillation unit was decompressed to a degree of vacuum of 4 hPa, and the reaction liquid obtained above was transported to the flask by compression transportation from the autoclave. Unreacted propyleneoxide was diffused for 30 minutes at an internal temperature of 40 to 50 degrees C., while bubbling of air was carried out at 3 mL/min. The acid component of the obtained reaction liquid gave 0.03 wt % (molar ratio of the acid component to the catalyst: 0.03). Then, the obtained reaction liquid was refined by distillation for 3 hours at an internal temperature of 50 to 90 degrees C., and 69.5 g of a reaction liquid after evaporation of the hydroxypropyl methacrylate therefrom was obtained. The acid component of the obtained reaction liquid gave 0.03 wt % (molar ratio of the acid component to the catalyst: 0.03).

<Recycling Reaction 2>

The reaction liquid after evaporation of hydroxypropyl methacrylate therefrom 69.5 g, and a part of 67.5 g in a total amount of supply of 369 g of methacrylic acid were introduced into an autoclave of a volume of 1 L made of SUS316 with a stirrer. The interior of the autoclave was replaced with nitrogen gas, subsequently, the temperature was raised up to 85 degrees C., and the internal pressure was adjusted to 0.05 MPa (G). Propyleneoxide was supplied by 128 g/h for 0.4 hour (50 g), then methacrylic acid by 187.5 g/h (301.5 g), and propyleneoxide by 128 g/h (206 g) were supplied for 1.6 hours, and a temperature of 85 degrees C. was maintained in the meantime, and the reaction was performed.

The reaction temperature after termination of supply of methacrylic acid and propyleneoxide was maintained constant at 85 degrees C., and the reaction was continued until the concentration (measurement by neutralization titration) of the acid component as methacrylic acid gave 0.10 wt %. Then the concentration of the acid component after continuation of the reaction of 1.6 hours gave 0.10 wt %.

Comparative Example 1-3

Fresh Reaction

A part of 137 g in a total amount of supply of 410 g of methacrylic acid, chromium acetate 2.46 g (0.010 mol) as a catalyst, hydroquinone monomethyl ether 0.41 g as a polymerization inhibitor were introduced into an autoclave of a volume 1 L made of SUS316 with a stirrer. The interior of the autoclave was replaced with nitrogen gas, subsequently, the temperature was raised up to 85 degrees C., and the internal pressure was adjusted to 0.05 MPa (G). Propyleneoxide was supplied at 145 g/h for 0.7 hour (102 g), then methacrylic acid at 212 g/h (273 g), and propyleneoxide at 145 g/h (188 g) were supplied for 1.3 hours, and a temperature of 85 degrees C. was maintained in the meantime, and the reaction was performed. The reaction temperature after termination of supply of methacrylic acid and propyleneoxide was maintained constant at 85 degrees C., and the reaction was continued until the concentration (measurement by neutralization titration) of the acid component as methacrylic acid gave 0.10 wt %. Then the concentration of the acid component after continuation of the reaction of 1.5 hours gave 0.10 wt %. The reaction liquid was cooled to a temperature not more than 30 degrees C. in 30 minutes (the reaction continuation period eventually gave 1.7 hours). The acid component of the obtained reaction liquid gave 0.005 wt % (the molar ratio of the acid component to the catalyst: 0.006).

Subsequently, a glass round bottom flask of a volume of 1 L fitted in a vacuum distillation unit was decompressed to a degree of vacuum of 4 hPa, and the reaction liquid obtained above was transported to the flask by compression transportation from the autoclave. Unreacted propyleneoxide was diffused for 30 minutes at an internal temperature of 40 to 50 degrees C., while bubbling of air was carried out at 3 mL/min. The acid component of the obtained reaction liquid gave 0.005 wt % (the molar ratio of the acid component to the catalyst: 0.006). Then, the obtained reaction liquid was refined by distillation for 3 hours at an internal temperature of 50 to 90 degrees C., and 69.5 g of a reaction liquid after evaporation of the hydroxypropyl methacrylate therefrom was obtained. The acid component of the obtained reaction liquid gave 0.005 wt % (the molar ratio of the acid component to the catalyst: 0.006).

<Recycling Reaction 1>

The reaction liquid after evaporation of hydroxypropyl methacrylate therefrom 69.5 g, and a part of 67.5 g in a total amount of supply of 369 g of methacrylic acid were introduced into an autoclave of a volume of 1 L made of SUS316 with a stirrer. The interior of the autoclave was replaced with nitrogen gas, subsequently, the temperature was raised up to 85 degrees C., and the internal pressure was adjusted to 0.05 MPa (G). Propyleneoxide was supplied at 131 g/h for 0.4 hour (50 g), then methacrylic acid at 187.5 g/h (301.5 g), and propyleneoxide at 131 g/h (211 g) were supplied for 1.6 hours, and a temperature of 85 degrees C. was maintained in the meantime, and the reaction was performed. The reaction temperature after termination of supply of methacrylic acid and propyleneoxide was maintained constant at 85 degrees C., and the reaction was continued until the concentration (measurement by neutralization titration) of the acid component as methacrylic acid gave 0.10 wt %. Then the concentration of the acid component after continuation of the reaction of 1.6 hours gave 0.10 wt %. The reaction liquid was cooled to a temperature not more than 30 degrees C. in 30 minutes (the reaction continuation period eventually gave 1.8 hours). The acid component of the obtained reaction liquid gave 0.005 wt % (the molar ratio of the acid component to the catalyst: 0.006).

Subsequently, a glass round bottom flask of a volume of 1 L fitted in a vacuum distillation unit was decompressed to a degree of vacuum of 4 hPa, and the reaction liquid obtained above was transported to the flask by compression transportation from the autoclave. Unreacted propyleneoxide was diffused for 30 minutes at an internal temperature of 40 to 50 degrees C., while bubbling of air was carried out at 3 mL/min. The acid component of the obtained reaction liquid gave 0.005 wt % (the molar ratio of the acid component to the catalyst: 0.006). Then, the obtained reaction liquid was refined by distillation for 3 hours at an internal temperature of 50 to 90 degrees C., and 69.5 g of a reaction liquid after evaporation of the hydroxypropyl methacrylate therefrom was obtained. The acid component of the obtained reaction liquid gave 0.005 wt % (the molar ratio of the acid component to the catalyst: 0.006).

<Recycling Reaction 2>

The reaction liquid after evaporation of hydroxypropyl methacrylate therefrom 69.5 g, and a part of 67.5 g in a total amount of supply of 369 g of methacrylic acid were introduced into an autoclave of a volume of 1 L made of SUS316 with a stirrer. The interior of the autoclave was replaced with nitrogen gas, subsequently, the temperature was raised up to 85 degrees C., and the internal pressure was adjusted to 0.05 MPa (G). Propyleneoxide was supplied at 128 g/h for 0.4 hour (50 g), then methacrylic acid at 187.5 g/h (301.5 g), and propyleneoxide at 128 g/h (206 g) were supplied for 1.6 hours, and a temperature of 85 degrees C. was maintained in the meantime, and the reaction was performed.

The reaction temperature after termination of supply of methacrylic acid and propyleneoxide was maintained constant at 85 degrees C., and the reaction was continued until the concentration (measurement by neutralization titration) of the acid component as methacrylic acid gave 0.10 wt %. Then the concentration of the acid component after continuation of the reaction of 1.8 hours gave 0.10 wt %.

As compared with Example 1-4, a gradually prolonged period of time until a concentration of the acid component gives 0.10 wt % shows a tendency of decrease of catalytic activity.

Example 2-1

Hydroxyethyl acrylate 225 g containing 28.4 wt % (0.400 mol) of diethylene glycol monoacrylate, a part of 48 g in a total amount of supply of 682 g of acrylic acid, chromium acetate 5.0 g (0.020 mol) as a catalyst (a molar ratio of diethylene-glycol monoacrylate to chromium acetate: 20), and phenothiazine 0.42 g as a polymerization inhibitor were introduced into an autoclave of a volume of 2 L made of SUS316 with a stirrer. The interior of the autoclave was replaced with nitrogen gas, subsequently, the temperature was raised up to 85 degrees C., and the internal pressure was adjusted to 0.05 MPa (G). Ethyleneoxide was supplied at 218 g/h for 10 minutes (36 g), then acrylic acid at 328 g/h (634 g), and ethyleneoxide at 218 g/h (400 g) were supplied for 110 minutes and a temperature of 85 degrees C. was maintained in the meantime, and the reaction was performed. The reaction temperature after termination of supply of acrylic acid and ethyleneoxide was maintained constant at 85 degrees C., the reaction was continued until the concentration (measurement by neutralization titration) of the acid component as acrylic acid gave 0.10 wt %. Then the concentration of the acid component after continuation of the reaction of 60 minutes gave 0.10 wt %. The reaction liquid was cooled to a room temperature (the reaction continuation period eventually gave 70 minutes).

Analysis by gas chromatography of the obtained reaction liquid gave 8.5 wt % (0.716 mol) of diethylene glycol monoacrylate concentration. This result showed that the concentration of diethylene glycol monoacrylate newly formed during the reaction was 3.75 wt % (0.316 mol) (diethylene-glycol monoacrylate selectivity based on acrylic acid: 3.3 mol %).

Comparative Example 2-1

A part of 272 g in a total amount of supply of 816 g of acrylic acid, chromium acetate 5.0 g (0.020 mol) as a catalyst (a molar ratio of diethylene-glycol monoacrylate to chromium acetate: 0), and phenothiazine 0.42 g as a polymerization inhibitor were introduced into an autoclave of a volume 2 L made of SUS316 with a stirrer. The interior of the autoclave was replaced with nitrogen gas, subsequently, the temperature was raised up to 85 degrees C., and the internal pressure was adjusted to 0.05 MPa (G). Ethyleneoxide was supplied at 264 g/h for 45 minutes (198 g), then acrylic acid at 471 g/h (589 g), and ethyleneoxide at 264 g/h (329 g) were supplied for 75 minutes, and a temperature of 85 degrees C. was maintained in the meantime, and the reaction was performed. The reaction temperature after termination of supply of acrylic acid and ethyleneoxide was maintained constant at 85 degrees C., the reaction was continued until the concentration (measurement by neutralization titration) of the acid component as acrylic acid gave 0.10 wt %. Then the concentration of the acid component after continuation of the reaction of 70 minutes gave 0.10 wt %. The reaction liquid was cooled to a room temperature (the reaction continuation period eventually gave 80 minutes).

Analysis by gas chromatography of the obtained reaction liquid gave 6.2 wt % (0.523 mol) of newly formed diethylene glycol monoacrylate concentration during reaction (diethylene-glycol monoacrylate selectivity based on acrylic acid: 4.6 mol %).

Comparative Example 2-2

Hydroxyethyl acrylate 225 g containing 2.2 wt % (0.031 mol) of diethylene glycol monoacrylate, a part of 48 g in a total amount of supply of 682 g of acrylic acid, chromium acetate 5.0 g (0.020 mol) as a catalyst (a molar ratio of diethylene-glycol monoacrylate to chromium acetate: 1.5), and phenothiazine 0.42 g as a polymerization inhibitor were introduced into an autoclave of a volume of 2 L made of SUS316 with a stirrer. The interior of the autoclave was replaced with nitrogen gas, subsequently, the temperature was raised up to 85 degrees C., and the internal pressure was adjusted to 0.05 MPa (G).

Ethyleneoxide was supplied at 221 g/h for 10 minutes (37 g), then acrylic acid at 328 g/h (634 g), and ethyleneoxide at 221 g/h (405 g) were supplied for 110 minutes, and a temperature of 85 degrees C. was maintained in the meantime, and the reaction was performed. The reaction temperature after termination of supply of acrylic acid and ethyleneoxide was maintained constant at 85 degrees C., the reaction was continued until the concentration (measurement by neutralization titration) of the acid component as acrylic acid gave 0.10 wt %. Then the concentration of the acid component after continuation of the reaction of 65 minutes gave 0.10 wt %. The reaction liquid was cooled to room temperature (the reaction continuation period eventually gave 75 minutes).

Analysis by gas chromatography of the obtained reaction liquid gave 6.0 wt % (0.507 mol) of diethylene glycol monoacrylate concentration. This result showed that the concentration of diethylene glycol monoacrylate newly formed during the reaction was 5.63 wt % (0.476 mol) (diethylene-glycol monoacrylate selectivity based on acrylic acid: 5.0 mol %).

Example 2-2

A glass round bottom flask of a volume of 1 L fitted in a vacuum distillation unit was decompressed to a degree of vacuum of 4 hPa, and the reaction liquid obtained in Example 2-1 1100 g was transported to the flask by compression transportation from the autoclave. Unreacted ethyleneoxide was diffused for 30 minutes at an internal temperature of 40 to 50 degrees C., while bubbling of air was carried out at 3 mL/min. Then, the obtained reaction liquid was refined by distillation for 3 hours at an internal temperature of 50 to 90 degrees C., and 275 g of a reaction liquid after evaporation of the hydroxyethyl acrylate therefrom was obtained. Analysis by gas chromatography of the obtained reaction liquid gave 27.6 wt % of diethylene glycol monoacrylate concentration.

Then, following reactions were newly performed. The reaction liquid after evaporation of hydroxyethyl acrylate therefrom 225 g (diethylene-glycol monoacrylate: 27.6 wt % (0.388 mol), chromium acetate: calculatively 3.3 g), a part of 48 g in a total amount of supply of 682 g of acrylic acid, chromium acetate as a catalyst 1.7 g (0.020 mol) (a molar ratio of diethylene-glycol monoacrylate to chromium acetate: 19), and phenothiazine 0.42 g as a polymerization inhibitor were introduced into an autoclave of a volume of 2 L made of SUS316 with a stirrer. The interior of the autoclave was replaced with nitrogen gas, subsequently, the temperature was raised up to 85 degrees C., and the internal pressure was adjusted to 0.05 MPa (G).

Ethyleneoxide was supplied at 218 g/h for 10 minutes (36 g), then acrylic acid at 328 g/h (634 g), and ethyleneoxide at 218 g/h (400 g) were supplied for 110 minutes, and a temperature of 85 degrees C. was maintained in the meantime, and the reaction was performed. The reaction temperature after termination of supply of acrylic acid and ethyleneoxide was maintained constant at 85 degrees C., the reaction was continued until the concentration (measurement by neutralization titration) of the acid component as acrylic acid gave 0.10 wt %. Then the concentration of the acid component after continuation of the reaction of 60 minutes gave 0.10 wt %. The reaction liquid was cooled to room temperature (the reaction continuation period eventually gave 70 minutes).

Analysis by gas chromatography of the obtained reaction liquid gave 8.4 wt % (0.707 mol) of diethylene glycol monoacrylate concentration. This result showed that the concentration of diethylene glycol monoacrylate newly formed during the reaction was 3.80 wt % (0.319 mol) (diethylene-glycol monoacrylate selectivity based on acrylic acid: 3.4 mol %).

INDUSTRIAL APPLICABILITY

The producing process of the present invention is preferred as a producing process having advantageous production costs of hydroxyalkyl(meth)acrylate. The present invention can provide a producing process for hydroxyalkyl(meth)acrylate allowing lower production costs. In detail, efficient recycling use of a catalyst once used for a reaction to the subsequent reaction in the amount used, activity and the like, or effective suppression of formation of a biadduct (dialkylene glycol mono(meth)acrylate) as a by-product can easily provide a producing process of hydroxyalkyl(meth)acrylate allowing lower production costs.

The invention claimed is:

1. A process for producing a hydroxyalkyl(meth)acrylate which comprises reacting a (meth)acrylic acid with an alkylene oxide in the presence of a catalyst in a reaction liquid, a condition wherein an amount of an acid component gives a value calculatively not less than 0.010 in terms of a molar ratio to an amount of the catalyst being maintained not only during the reaction, but in cooling in the end of the reaction, in a standby period until evaporation of the hydroxyalkyl (meth)acrylate product, and in and after evaporation of the hydroxyalkyl(meth)acrylate product, a reaction liquid after evaporation of the hydroxyalkyl(meth)acrylate therefrom is used for a subsequent reaction, and the catalyst is a homogeneous catalyst that is chromium (Cr) compound.

2. The process for producing a hydroxyalkyl(meth)acrylate according to claim 1, wherein 20 to 90% by weight in the reaction liquid after evaporation of the hydroxyalkyl(meth) acrylate therefrom is used for the subsequent reaction.

3. The process for producing a hydroxyalkyl(meth)acrylate according to claim 1, wherein the homogeneous catalyst is soluble in the reaction liquid including the (meth)acrylic acid and the alkylene oxide.

* * * * *